(12) United States Patent
Wagner et al.

(10) Patent No.: US 6,348,964 B1
(45) Date of Patent: Feb. 19, 2002

(54) VIEWER FOR GEMSTONES

(76) Inventors: Randall M. Wagner, 12433 Madero Dr., Mequon, WI (US) 53092; Kurt Schoeckert, 4876 Rolling Hills Dr., Hartford, WI (US) 53027

(*) Notice: Subject to any disclaimer, the term of this patent is extended or adjusted under 35 U.S.C. 154(b) by 0 days.

(21) Appl. No.: 09/382,961

(22) Filed: Aug. 25, 1999

(51) Int. Cl.$^7$ ............................................. G01N 21/00
(52) U.S. Cl. ............................................. 356/30; 356/425
(58) Field of Search ........................... 356/30, 31, 425; 359/387, 803–816

(56) References Cited

U.S. PATENT DOCUMENTS

| | | | | |
|---|---|---|---|---|
| 3,989,379 A | * | 11/1976 | Eickhorst | 356/30 |
| 5,430,538 A | * | 7/1995 | Kobayashi | 356/30 |
| 5,615,005 A | | 3/1997 | Valente et al. | 356/30 |
| 5,811,817 A | * | 9/1998 | Ravich | 356/30 |
| 6,020,954 A | * | 2/2000 | Aggarwal | 356/30 |

FOREIGN PATENT DOCUMENTS

| | | |
|---|---|---|
| EP | 464824 A3 | 1/1992 |
| GB | 2110416 A | 6/1983 |
| WO | 9623207 A1 | 8/1996 |

* cited by examiner

*Primary Examiner*—Frank G. Font
*Assistant Examiner*—Roy M. Punnoose
(74) *Attorney, Agent, or Firm*—William K. Baxter; Godfrey & Kahn, S.C.

(57) ABSTRACT

A viewer for gemstones allowing a person to view the light performance of a gemstone having a 360-degree light unit positioned above a base where the stone is placed. The light unit is attached to an adjustable mounting bracket which allows the bracket and light unit to move vertically through use of a control mechanism. The base allows for secure and consistent placement of the gemstone, and positioning of a light control structure, preferably made from a reflective material, over the stone. The position of the stone is under the center of the light unit and light control structure. The light control structure has an aperture to allow the light from the light unit to enter.

18 Claims, 3 Drawing Sheets

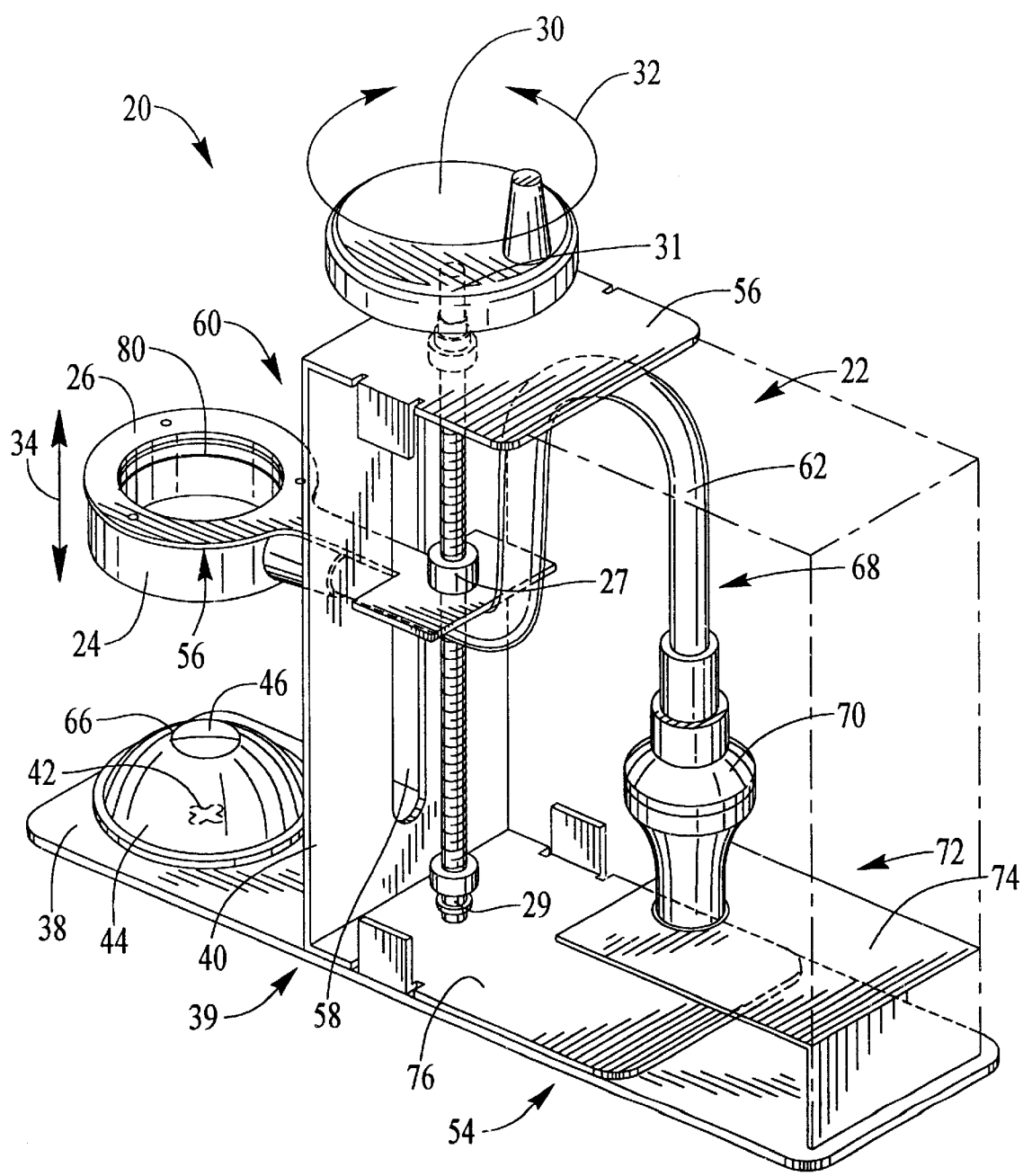
FIG_1

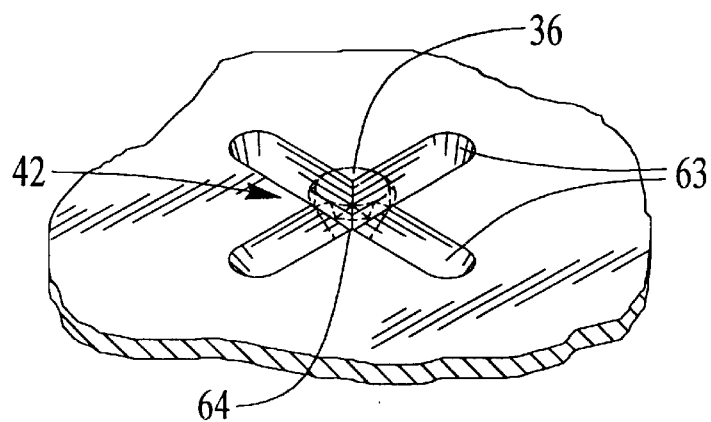
FIG_2
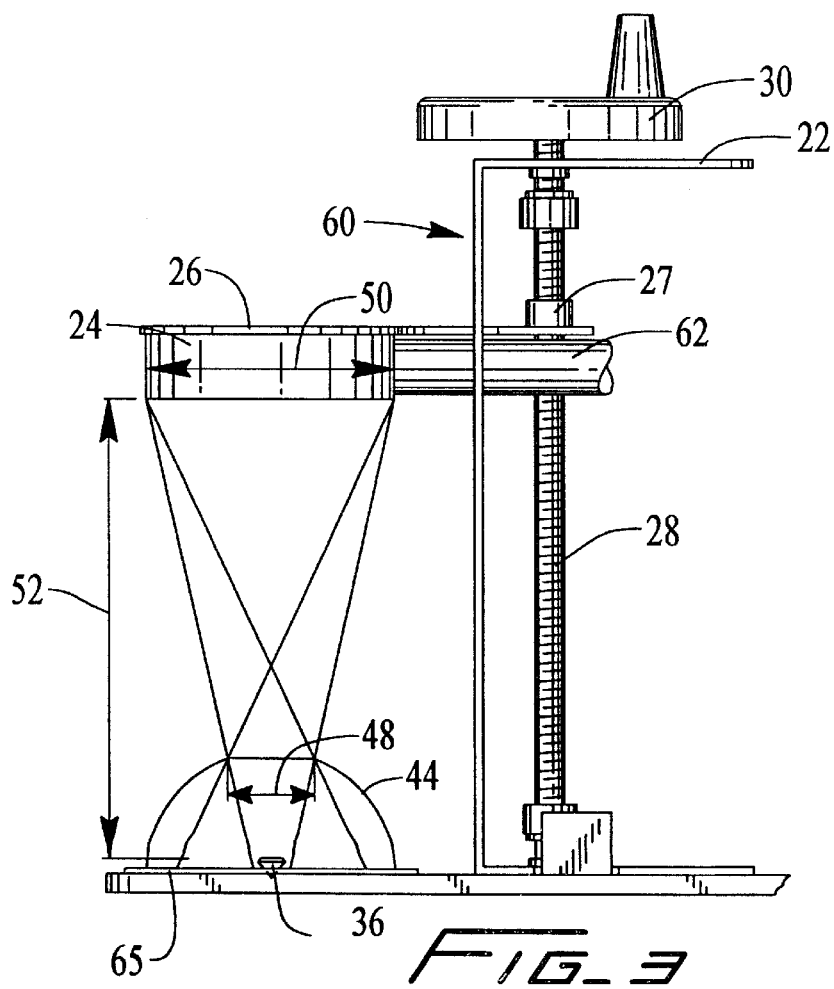
FIG_3

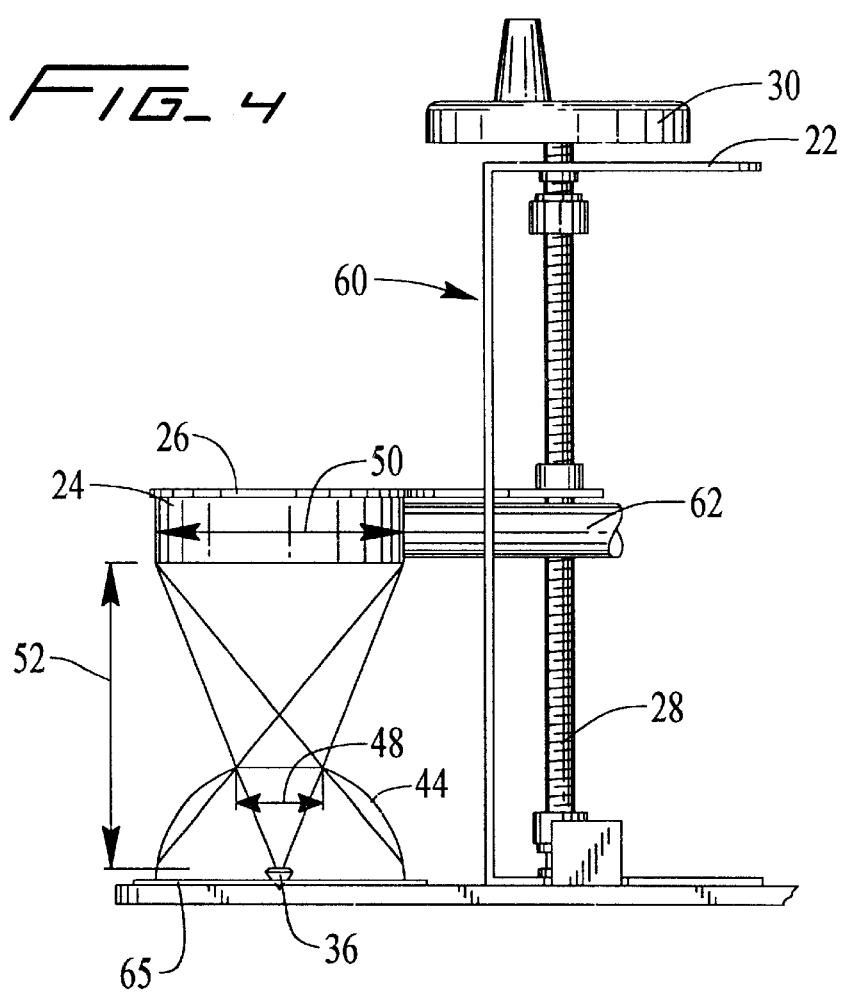
FIG_4
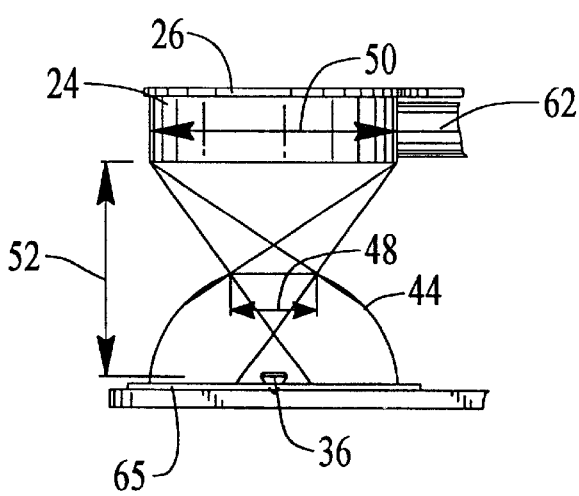
FIG_5
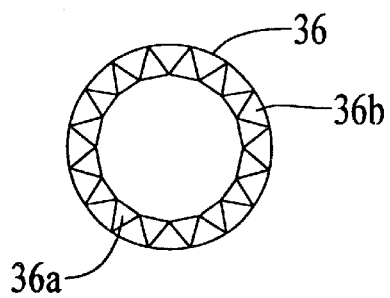
FIG_6

VIEWER FOR GEMSTONES

BACKGROUND OF THE INVENTION

This invention relates generally to devices used to evaluate gemstones and, more particularly, to devices and methods that permit the light performance of a gemstone to be evaluated.

The commercial value of a gemstone depends upon the gemstone weight, cut, clarity and color. Each characteristic has an effect on the price of the gemstone. Thus the evaluation of these parameters is critical to setting the price. Weight is measured objectively, clarity is a subjective measurement made by evaluating the inclusions through a microscope, and color is evaluated subjectively against a master color set. Currently cut is evaluated by measuring the cut angles and comparing the angles to a theoretical ideal standard. If the cut angles approach the ideal standard, in theory the gemstone, particularly a diamond, will have high brilliance and dispersive characteristics otherwise known as brilliancy or light performance.

When illuminated, a diamond returns light in the form of white light and colored light at various intensities. Sparkle is the result of light being reflected and refracted by the stone and is considered to be a major factor in a stone's beauty. Other contributing factors in a stone's, particularly a diamond's, beauty include brilliance, scintillation, fire, and brightness. These factors taken together describe the light performance of a gemstone.

When purchasing a diamond, to evaluate its light performance, and therefore its beauty, standard practice calls for tilting the diamond in a well-lit room or under a diamond light to change the angle that the light enters the stone. This causes the stone to sparkle but is generally an insufficient method to demonstrate its beauty.

U.S. Pat. No. 5,615,005, issued to Valente et al., provides a device and method for grading gemstones. The device utilizes a band pass filter and detector array to obtain the spectral response of a complete image. The image of the gemstone is transmitted through a processing system which includes sequential selection of individual wavelengths, detecting the amplitude of each wavelength, and converting the amplitude signal into a form for subsequent processing. While effective, this method may prove to be expensive and perform functionally beyond what may be desired.

Accordingly, a need exists for an improved device and method for viewing stones, and more specifically, diamonds, prior to purchase. Further, there is a need to be able to view and compare the light performance of diamonds prior to purchase in a controlled and consistent manner. Further, there is a need for controlled and consistent viewing and evaluation of light performance at the point of purchase. It would also be desirable to have a relatively inexpensive device for evaluating light performance.

SUMMARY OF THE INVENTION

Therefore, it is an object of the present invention to provide a device for viewing gemstones, and in particular, diamonds. It is an additional object of the present invention to provide a diamond-viewing device that enables viewing in a controlled and consistent manner and which enables one to better view a diamond's beauty. It is a further object of the present invention to provide a diamond-viewing device that allows such viewing to be readily available at the point of purchase. It is a further object of the present invention to provide a diamond-viewing device that is efficient and relatively inexpensive for the diamond seller to have on hand. It is a further object of the present invention to provide a diamond-viewing device that overcomes the disadvantages of the prior art.

The diamond viewer of the present invention provides the above-mentioned and many additional objects by providing a diamond viewer that allows a person to view the light performance of a diamond, and therefore its beauty, in a controlled environment. The diamond viewer allows viewing of the light performance of a diamond by controlling the light used for viewing to be consistent (which also aids in side-by-side evaluations), by changing the angle by which the light enters the stone by means of a moveable light source above the diamond, as well as placing the diamond within a light control structure or other light control structure, preferably made of reflective material, to better see the diamond's secondary colors and sparkle.

The diamond viewer of the present invention has a light unit attached to a mounting bracket. The mounting bracket is dependent from a threaded shaft that transmits rotational movement of a hand wheel into vertical movement, allowing the mounting bracket and light ring to move vertically. A base is provided to allow for secure and consistent placement of a diamond during viewing. As indicated, a light control structure is positioned over the diamond. An aperture is formed in the light control structure to allow light from the light unit to enter. The diamond is positioned under the center of the light unit and light control structure. The light control structure is opaque, and shaped with an aperture in its top such as to create proper lighting angles to enhance the diamond's sparkle and beauty during viewing. The angle at which the light illuminates the diamond is produced by a combination of factors, namely the size of the aperture in the light control structure, the diameter of the light unit, and the distance between the light unit and the diamond.

The diamond viewer functions when the user places the diamond under the light control structure. Light from the light unit positioned above the light control structure enters the diamond through the aperture in the light control structure. As stated, the angle at which the light hits the diamond is governed by the relative size of the aperture in the light control structure, the diameter of the light unit, and the distance from the light unit to the diamond. The light unit can be vertically repositioned by use of the hand wheel. By then viewing the diamond, the purchaser is better able to see the diamond's sparkle, and overall light performance, in a controlled and consistent setting.

As mentioned, currently to evaluate a diamond's beauty when purchasing, a user would tilt a diamond in a well-lit room or under a diamond light. By tilting the stone, essentially the user is changing the angle that the light enters the stone. This method is confusing to the customer and does an inconsistent job showing the diamond's beauty. The diamond viewer allows a person to view the light performance of a diamond in a consistent manner. The diamond viewer changes the angle that the light enters the stone by moving the vertical position of a light source above the diamond. Because the diamond viewer places the diamond in a controlled lighting environment, the diamond sparkles in a more brilliant manner. A person can then evaluate how beautiful a diamond is and make a value/price decision.

The diamond viewer is advantageous to both the retailer and the consumer. The device will illuminate the diamond in such a way that the diamond's directly refracted light (i.e., white light), as well as the dispersed light (i.e., spectral colors) are readily available to the consumer. This will, of course, also enable the consumer to better make a value/ price decision, and to understand why price and certificates are not the only consideration. And, because the retailer is able to more easily demonstrate the beauty of the diamond, the invention will allow the retailer to more easily and better explain the correlation of price and value, and, subsequently, sell more high-end center stones.

While the present invention can be used to view diamonds at point of consumption, it should be noted that the present invention could be adapted for viewing other stones at various points in their evaluation process.

In sum, the present invention represents a significant improvement over the prior art in many ways. The diamond viewer in accordance with the present invention allows for controlled and efficient diamond viewing at the point of consumption, and overcomes the disadvantages of the prior art. These and other objects and advantages of the present invention will become apparent from the detailed description and accompanying drawings.

DESCRIPTION OF THE DRAWINGS

FIG. 1 is a perspective view of a diamond viewer (with the shell shown in phantom) constructed according to an embodiment of the present invention;

FIG. 2 is a partial perspective view of the support holder of the diamond viewer of FIG. 1, shown on an enlarged scale;

FIG. 3 is a side view of the diamond viewer of FIG. 1 illustrating the lighting patterns created when the light unit is in a raised position; and FIG. 4 is a side view of the diamond viewer of FIG. 1 illustrating the lighting patterns created when the light unit is in a lowered position.

FIG. 5 is a partial side view of the diamond viewer of FIG. 1 illustrating the lighting patterns created when the light unit is further lowered such as to create a diffuse lighting position, where no direct light hits the table of the stone.

FIG. 6 is a top view of a diamond as it would look with the light unit in the position shown in FIG. 5.

DESCRIPTION OF THE PREFERRED EMBODIMENTS

A diamond viewer 20 prepared according to a preferred embodiment of the present invention is shown generally in FIG. 1, with an outer shell 22 shown partially in phantom.

The diamond viewer 20 includes a base 38 upon which a diamond 36 is placed for viewing. The base 38 extends from the lower-front portion 40 of the generally rectangularly-shaped outer shell 22. A gem support or holder 42, shown best in FIG. 2, is typically formed, such as by machining, into the base 38 to allow for proper and consistent placement of the diamond 36. As shown in FIG. 2, in the preferred embodiment the gem support 42 is formed by machining two intersecting grooves, with the diamond 36 being placed at the intersection of those grooves. A light control structure 44, of any suitable shape, is placed on top of the base 38 over the diamond 36. The light control structure 44 includes an aperture 46 machined or otherwise formed into the light control structure 44, generally in the center thereof. The light control structure 44 is positioned on the base 38 so that the diamond 36 is generally aligned under the aperture 46.

The present invention diamond-viewing apparatus can be placed directly on a counter-top, or such, at the retailer's place of sale. The base 38 has a bottom surface 54 which may have feet or cushions (not shown) to allow for more stable placement.

As indicated above, an outer shell 22 extends up from the base 38 to enclose a portion of the viewer 20. The outer shell 22, in combination with the base 38, will typically form an enclosed rectangular solid shape. The outer shell 22 may contain a second base 76, or a portion thereof, which will fit upon, and attach to, base 38 for further support and ease of production of the device. The outer shell 22 also has a front portion 60 which forms an upright standard extending upward from the base 38 at a location 39 positioned inward from one end of the base 38.

The invention also provides an adjustable support mechanism. In the preferred embodiment, a vertically-positioned threaded shaft 28 is mounted in the enclosed portion of the shell 22. Threaded onto shaft 28 is a nut 27. A mounting bracket 26 is affixed to or integrally formed with the nut 27. The threaded shaft 28 thereby transmits rotational movement, as shown by arrow 32, into vertical movement of the mounting bracket 26, as shown by arrow 34, allowing the mounting bracket 26 and an attached light unit 24 (discussed in greater detail below) to move vertically above the diamond 36 for optimum viewing. The bottom 29 of the threaded shaft 28 is rotatably attached to base 38 (or second base 76). The threaded shaft 28 extends vertically to the top of the outer shell 22. Affixed to the top 31 of the threaded shaft 28 is a hand wheel 30. The hand wheel 30 extends from the threaded shaft 28 and is accessible from the top 56 of the outer shell 22. The turning motion of the hand wheel 30 controls the rotational movement of the threaded shaft 28, and thus, the vertical movement of the mounting bracket 26 and its attached light unit 24.

The mounting bracket 26 connects to the threaded shaft 28 through a slot 58 cut into the front portion 60 of the shell 22. The slot 58 allows the mounting bracket 26, light unit 24, and light tube 62 (discussed in greater detail below) to move vertically along the threaded shaft 28. The slot 58 is preferably positioned up from the bottom of the shell at least as high as the top 66 of the light control structure 44, so as to avoid contact between the light unit 24 and the light control structure 44, but still able to allow the light unit 24 in close enough proximity to allow diffused lighting.

The light unit 24 is positioned by the mounting bracket 26 in a generally horizontal plane above the base 38. In the preferred embodiment, the light ring is a 360 degree light ring. It may be possible, however, for the necessary light to be provided in different shapes or types. One example is a ring of light with evenly placed multiple lighting points. The important feature is that the light unit has an area, generally in the center, where no light is provided, the importance of which will be explained below. The light unit 24 is generally centered over the diamond 36 and the aperture 46 in the light control structure 44, and illuminates downward onto the diamond positioned on the gem support 42 on the base 38 below, assisting to create a geometry of reflecting light. The light unit 24 is typically attached to the underside 56 of the moveable mounting bracket 26 in order to optimize lighting angles. Gemstones are generally viewed by individuals from multiple angles, relative to light sources, to obtain scintillation or sparkle. The multiple position light source provides the device with the same capabilities.

For optimum analysis of highly reflective gemstones, the lighting geometry is selected to produce a position which prevents the light from directly reflecting off the surface of the gemstone. Refraction of light through a gemstone gives the diamond its sparkle. The angular position of the light unit prevents light from reflecting off this surface and distorting the analysis when it is in its uppermost position.

The light unit 24 is attached to the moveable mounting bracket 26 as such to provide multiple lighting angles for the scintillation analysis. The movement is designed such that the lighting positions can vary from a diffuse position (where no direct light hits the table of the stone), to a reflectance position (where the light beam is nearly centered on the stone).

As indicated above, as seen in FIG. 2, the support holder 42 may be machined into the base 38 to allow for consistent and secure placement of the diamond 36 on the base. In this embodiment, the support holder 42 is comprised of two v-shaped indentations 63 extending from a deeper sixty-degree counter-bore hole 64. The deeper center counter-bore hole 64 allows for placement of an oval diamond. The particular shape of hole 64 allows for efficient securement of various sizes and shapes of stones or settings. However, the support holder 42 can be any of a number of mechanisms used to secure the diamond in place, such as a mechanical claw or a spring-loaded clasp.

In this embodiment the light control structure 44 is removable, and is removed when placing the diamond 36 in its support holder 42. The light control structure 44 is then placed on top of the base 38 and positioned so as to cover the diamond 36 placed on the base 38. A counter-bore (not shown) is typically machined into the base into which the flange 65 of the light control structure will set. This will help to assure consistent and secure placement of the light control structure 44. As stated, the angle at which the light illuminates the diamond 36 is produced by a combination of factors, namely the size of the aperture in the top 66 of the light control structure (as shown by arrow 48), the diameter of the light ring (as shown by arrow 50), and the distance the light ring is from the diamond (as shown by arrow 52).

The light control structure 44 is preferably made of an opaque, reflective material such as a light, white plastic, a spectraflect-coated material, or a barium-coated material, and formed in the shape of a hemisphere. However, while the light control structure 44 may also be of generally any type of rigid material and will be functional in most situations, a reflective material will help to illuminate the diamond when the light unit is in a diffused lighting position, as shown in FIG. 5. The result of the use of the reflective material is that certain details of the diamond 36 will be able to be seen, as shown in FIG. 6. In particular, for certain cuts of diamond, this view will bring out the "hearts" 36a and "arrows" 36b of the diamond 36.

In the preferred embodiment the light unit 24 receives its light from light assembly 68, which is a fiber optic cable assembly providing an evenly distributed light to the light unit. Preferably the light unit 24 is an annular, 360 degrees light ring. As stated, it may be possible, though, for the light unit 24 to be other shapes and still be effective, as long as even lighting is transmitted. The important feature is that the light unit 24 have an area, generally in the center, where no light is sourced. The light unit 24 delivers the light generated from a light source 70, generally at least a 2100° Kelvin light source, which is generally located inside the lower-back portion 72 of the diamond viewer's shell 22. The light source 70 is typically supported by a support 74 extending up from the base 38 in the lower-back portion 72 of the shell 22. A light tube 62 runs from the light source 70 to the light unit 24. The light tube 62 extends from the front portion 60 of the shell 22 through slot 58 and is attached to the underside 56 of the mounting bracket 26 to move in conjunction with the mounting bracket 26 and light unit 24.

To mount and view a diamond 36 with the diamond viewer 20, the diamond is first positioned in the support holder 42 on the base 38. The light control structure 44 is then placed atop the base 38, aligning the aperture 46 in its top surface 66 with that of the above light unit 24. By rotation of the hand wheel 30 one can adjust the vertical position of the light unit 24 in order to further optimize the sparkle and beauty of the diamond.

In an alternative embodiment, a magnifying lens 80 may be installed to better view the diamond. The magnifying lens 80 would typically be positioned above the light control structure 44, but not in the way of the light. For example, it could be positioned such as that shown in FIG. 1, where the magnifying lens 80 is located within the light unit 24.

Although the invention has been herein shown and described in what is perceived to be the most practical and preferred embodiments, it is to be understood that the invention is not intended to be limited to those specific embodiments. Rather, it is recognized that modifications may be made by one of skill in the art without departing from the spirit or intent of the invention. Therefore, the invention is to be taken as including all reasonable equivalents to the subject matter of the appended claims.

We claim:

1. A gemstone viewer comprising:

a base having a gemstone holder;

a support mechanism coupled to the base for supporting a vertically adjustable mounting bracket and a light assembly;

a vertically adjustable light unit mounted on the vertically adjustable mounting bracket of the support mechanism and positioned above the gemstone holder of the base; and a light control structure placed on the base over the gemstone holder, the light control structure having an aperture formed in the center thereof for viewing a gemstone placed in the gemstone holder of the base.

2. The device of claim 1, wherein the light unit comprises an annular light ring creating consistent uniform lighting.

3. The device of claim 1, wherein the support mechanism further comprises a threaded shaft with a control mechanism connected thereto, and wherein the mounting bracket is dependent from the threaded shaft which translates rotational movement of the control mechanism into vertical movement of the mounting bracket.

4. The device of claim 1, wherein the light assembly comprises a light source coupled to the light unit through a light tube.

5. The device of claim 1, wherein the gemstone holder comprises at least one indentation machined into the base.

6. The device of claim 1, wherein the light control structure assists to create a geometry of reflecting light.

7. The device of claim 1, wherein the light control structure is made of a reflective material for reflecting light toward the gemstone placed in the gemstone holder of the base.

8. A device for viewing the light performance of a gemstone comprising:

a base having a gemstone holder;

a light control structure placed on the base over the gemstone holder, the light control structure having an aperture formed in the center thereof, for viewing a gemstone placed in the gemstone holder of the base;

a vertically adjustable light unit mounted on a vertically adjustable mounting bracket above the gemstone holder of the base; and a support mechanism coupled to the base for supporting the vertically adjustable mounting bracket, the support mechanism having a control mechanism for controlling the vertical position of the light unit above the gemstone holder of the base.

9. The device of claim 8, wherein the light unit comprises an annular light ring.

10. The device of claim 8, wherein the support mechanism further comprises a threaded shaft with the control mechanism connected thereto, and wherein the mounting bracket is dependent from the threaded shaft which translates rotational movement of the control mechanism into vertical movement of the mounting bracket.

11. The device of claim 9, wherein the annular light ring is attached to the vertically adjustable mounting bracket.

12. The device of claim 8, further comprising a magnifying lens attached to the mounting bracket above the light unit.

13. The device of claim 8, wherein the light unit is coupled to a light source through a light tube.

14. The device of claims 8, wherein the light control structure is made of a reflective material for reflecting light toward the gemstone placed in the gemstone holder.

15. A method of viewing the light performance characteristic of a gemstone using a viewing device, the method comprising the steps of:

placing the gemstone onto a base of the viewing device;

positioning a light control structure onto the base of the viewing device over the gemstone, the light control structure having an aperture in its center directly above the gemstone through which to view the gemstone;

positioning a vertically adjustable light unit attached to a mounting bracket on a support mechanism above the light control structure; and adjusting the vertical position of the light unit above the light control structure in order to display the light performance of the gemstone.

16. The method as defined by claim 15, wherein the step of placing the gemstone onto the base is carried out by placing the gemstone into a gemstone holder machined into the base for securement of the gemstone.

17. The method as defined by claim 15, further comprising the step of adjusting a control mechanism on the support mechanism to adjust the vertical position of the light unit above the gemstone for viewing the gemstone through the light unit as the vertical position of the light unit is adjusted above the gemstone.

18. The method as defined by claim 15, further comprising the step of viewing the gemstone through a magnifying glass attached to the mounting bracket above the light unit.

* * * * *